(12) United States Patent
Nemori et al.

(10) Patent No.: US 7,067,272 B2
(45) Date of Patent: Jun. 27, 2006

(54) THIN MEMBRANE FOR MEASURING PROTEASE ACTIVITY

(75) Inventors: Ryoichi Nemori, Kanagawa (JP); Masayoshi Yamamoto, Kanagawa (JP); Kouki Nakamura, Kanagawa (JP); Yasunori Okada, Tokyo (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 437 days.

(21) Appl. No.: 10/239,499

(22) PCT Filed: Mar. 23, 2001

(86) PCT No.: PCT/JP01/02345

§ 371 (c)(1),
(2), (4) Date: Dec. 30, 2002

(87) PCT Pub. No.: WO01/71025

PCT Pub. Date: Sep. 27, 2001

(65) Prior Publication Data

US 2003/0148399 A1 Aug. 7, 2003

(30) Foreign Application Priority Data

Mar. 24, 2000 (JP) .............................. 2000-083176
Jun. 22, 2000 (JP) .............................. 2000-187061

(51) Int. Cl.
 *C12Q 1/37* (2006.01)
(52) U.S. Cl. .................... 435/23; 435/24; 435/68.1; 435/219
(58) Field of Classification Search ................ 435/23, 435/24, 68.1, 219; 422/57, 60
See application file for complete search history.

(56) References Cited

U.S. PATENT DOCUMENTS 6,485,926 B1 * 11/2002 Nemori et al. ................ 435/23
2003/0138432 A1 * 7/2003 Glazier .................... 424/178.1
2003/0165954 A1 * 9/2003 Katagiri et al. ................ 435/6
2004/0071687 A1 * 4/2004 Rafii et al. ............... 424/94.63

FOREIGN PATENT DOCUMENTS

EP 0 884 393 A1 12/1998
EP 1 085 097 A1 3/2001

OTHER PUBLICATIONS de la Paz, et al. Matrix Metalloproteinases and Their Inhibitors in Human Vitreous. Investigative Ophthalmology and Visual Science. 39(7)1256-1260, Jun. 1998.*
Yu, W. et al. Heparan Sulfate Proteoglycans as Extracellular Docking Molcules for Matrilysin (MMP7). J of Biological Chemistry 275(6)4183-4191, Feb. 2000.*
Monica A. De La Paz et al., "Matrix Metalloproteinases and Their Inhibitors in Human Vitreous", IVOS (1998) vol. 39, No. 7, pp. 1256-1260.
Wei-Hsuan Yu et al., "Heparan Sulfate Proteoglycans as Extracellular Docking Molecules for Matrilysin (Matrix Metalloproteinasse 7)", The Journal of Biological Chemistry (2000) vol. 275. No. 6, pp. 4183-4191.
Michiyasu Itoh et al., "Purification and Refolding of Recombinant Human proMMP-7 (pro-Matrilysin) Expressed in *Escherichia coli* and Its Characterization" J. Biochem. (1996) vol. 119, No. 4, pp. 667-673.
Hiroshige Nagaya et al., Examination of synovial fluid and serum hyaluronidase activity as a joint marker in rheumatoid arthritis and osteoarthritis patients (by zymography) Ann Rheum Dis (1999) vol. 58, No. 3 pp. 186-188.
Supplementary Partial European Search Report dated Jan. 5, 2005.
Y Adachi et al. "Contribution of matrilysin (MMP-7) to the metastatic pathway of human colorectal cancers" (1999) GUT, vol. 45, No. 2, pp. 252-258.
Carol A. Vater et al. "Purification of an Endogenous Activator of Procollagenaase from Rabbit Synovial Fibroblast Culture Medium" (1983) Journal of Biological Chemistry, vol. 258, No. 15, pp. 9374-9382.
Partial European Search Report dated Apr. 14, 2005.

* cited by examiner

*Primary Examiner*—Ralph Gitomer
(74) *Attorney, Agent, or Firm*—Sughrue Mion, PLLC

(57) ABSTRACT

A thin membrane for measuring protease activity, which is formed on a support and, which comprises one or more kinds of substances selected from the group consisting of a transferrin derivative and an albumin derivative and is crosslinked and/or substantially water-insoluble. The membrane enables selective measurement of protease activity of a particular class of protease such as matrix metalloproteinase 7.

17 Claims, No Drawings

THIN MEMBRANE FOR MEASURING PROTEASE ACTIVITY

This application is a national stage of international application PCT/JP01/02345, filed Mar. 23, 2001 which claims priority to Japan Application 2000-187061 filed Jun. 22, 2000, which claims priority to Japan Application 2000-83176 filed Mar. 24, 2000.

FIELD OF THE INVENTION

The present invention relates to a thin membrane for measuring protease activity and a method for measuring protease activity. More specifically, the present invention relates to a thin membrane for measuring protease activity and a method for measuring protease activity, which enable accurate diagnosis of, for example, malignancy of cancer cells such as infiltrative and metastatic activities, degree of progress of periodontal diseases such as alveolar pyorrhea, destructive pathological conditions in rheumatoid arthritis, arteriosclerotic lesion and the like.

RELATED ART

It is known that various proteases such as matrix metalloproteinases and plasminogen activator are involved in infiltration and metastasis of cancer cells, progress of periodontal diseases such as alveolar pyorrhea, progress of tissue destruction in rheumatoid arthritis and the like, wound healing process, ontogenesis process and the like. As methods for detecting and quantifying such proteases, immunoassay methods that utilize antibodies, immunoblotting methods and electrophoresis zymography methods and the like are known. Further, as a method for measuring protease activity in tissues, the so-called in situ zymography method is known, which is disclosed in Science, vol. 170, pp.749–751, The FASEB Journal, vol. 9, July, pp.974–980, 1995, International Patent Publication WO97/32035 or Japanese Patent Application No. 11-365074/1999.

WO97/32035 discloses a method of detecting a protease by using a thin membrane that contains a protease substrate and a hardening agent and is formed on a support. In this method, gelatin is used as a typical protease substrate, and a protease can be measured by observing traces of digestion formed by the protease on the gelatin thin membrane. Further, Science, vol. 170, pp.749–751, 1970 discloses a method of detecting a protease by using a thin membrane that contains gelatin and glutaraldehyde and is formed on a support. In this method, gelatin is used as a protease substrate, and a trypsin-like protease can be measured by measuring traces of digestion formed by the protease on the gelatin thin membrane.

However, when a gelatin thin membrane is used, the thin membrane may be digested by digestive enzymes, of for example, digestive tract tissues, as well as those of cancer cells, inflammatory cells and the like, because a plurality of proteases such as matrix metalloproteinases (also abbreviated herein as "MMP") 2, 3, 7, 9 and serine proteases (trypsin, plasmin and the like) have digestive activity for the thin membrane. For this reason, when gelatin is used as a protease substrate, a problem arises that activities of proteases relevant to diseases cannot be selectively detected.

Analytical Biochemistry, 176, pp.261–264, 1989 discloses that a protein, which is obtained by reducing disulfide bonds of bovine serum albumin and bonding colorants to the produced thiol groups, is allowed to adsorb on a membrane, and activities of cathepsin D, trypsin, chymotrypsin, and papain can be detected by using the membrane. However, the reference is silent about measurement of MMP.

Recently, MMP 7 has been focused as one of MMPs mainly secreted from cancer cells, and development of the method for the specific detection of MMP 7 has been desired.

DISCLOSURE OF THE INVENTION

An object of the present invention is to provide a thin membrane for measuring protease activity and a method for measuring protease activity, which enable accurate diagnosis of, for example, malignancy of cancer cells such as infiltrative and metastatic activity, degree of progress of periodontal diseases such as alveolar pyorrhea, destructive pathological conditions in rheumatoid arthritis, arteriosclerotic lesion and the like. More specifically, the object of the present invention is to provide a thin membrane for measuring protease activity on which traces of digestion are specifically formed by a particular class of protease, and a method for measuring protease activity using such a thin membrane. A further object of the present invention is to provide a thin membrane for measuring protease activity on which traces of digestion are specifically formed by MMP 7, and a method for measuring protease activity using such a thin membrane.

The inventors of the present invention conducted various studies to achieve the foregoing objects. As a result, they found that a thin membrane containing a substance selected from the group consisting of transferrin derivatives and albumin derivative as a protease substrate was hardly digested by a protease other than MMP 7 (such as MMP 2, MMP 3, MMP 9 and the like) as compared with a thin membrane containing gelatin. Further, they found that, based on the above fact, MMP 7 selectively formed traces of digestion on a thin membrane containing the aforementioned substance. The present invention was achieved on the basis of these findings.

The present invention thus provides a thin membrane for measuring protease activity, which is formed on a support and which comprises one or more kinds of substances selected from the group consisting of transferrin derivatives and albumin derivatives and is crosslinked and/or substantially water-insoluble.

As preferred embodiments of the thin membrane, provided are the aforementioned thin membrane, which further comprises a protease inhibitor, and the aforementioned thin membrane, which further comprises a hardening agent. As the protease inhibitor, a matrix metalloproteinase inhibitor, a serine protease inhibitor or a cysteine protease inhibitor is preferred. The thin membrane may have a monolayer structure or a multilayer structure.

As preferred embodiments of these thin membranes, provided are the aforementioned thin membranes, which further comprises a colorant, and the aforementioned thin membranes, which comprises a solid-dispersed or emulsion-dispersed colorant. As the colorant, a colorant exhibiting visible absorption or a fluorescent colorant is preferred. The colorant may be used alone or two or more kinds of the colorants may be used in combination. When the thin membrane consists of two or more layers, each layer may contain the same colorant or a different colorant.

As a more preferred embodiment of the thin membrane of the present invention, provided are the aforementioned thin membrane, which comprises a crosslinked transferrin derivative, preferably a transferrin derivative crosslinked with a hardening agent. Also provided are the aforementioned thin membrane, wherein the transferrin derivatives are those in which a substituent is introduced on a sulfur atom derived from a disulfide bond; and the aforementioned thin membrane, wherein the transferrin derivative is carboxymethyltransferrin.

The present invention further provides the aforementioned thin membrane, wherein the albumin derivatives are those in which a substituent is introduced on a sulfur atom derived from a disulfide bond; and the aforementioned thin membrane, wherein the albumin derivative is one or more derivatives selected from the group consisting of carboxymethylated serum albumin, N-alkylsuccinimidated serum albumin, and S-carboxymethylated conalbumin.

The thin membrane preferably has a thickness of 0.5 to 10 µm, and the membrane is preferably formed on a plastic or glass support and dried. As the protease, matrix metalloproteinase (MMP) 7 is preferred.

From another aspect of the present invention, provided is a method for measuring protease activity, which comprises the steps of:
(1) bringing a sample containing a protease into contact with the aforementioned thin membrane; and
(2) detecting a trace of digestion formed on the thin membrane by activity of the protease.

As preferred embodiments of the aforementioned method, provided are the aforementioned method, wherein the trace of digestion is detected after the thin membrane is washed; the aforementioned method, wherein the trace of digestion is detected after the thin membrane is stained with a dye; the aforementioned method, wherein the sample is a biosample containing a tissue slice or cells; and the aforementioned method, which comprises a step of staining a tissue slice or cell nuclei on the thin membrane with a dye of a color that enables distinction of the tissue slice or cell nuclei from the thin membrane. As a biological tissue, tissue slices, cells, body fluids or the like can be used. For example, after a sample is brought into contact with the thin membrane, the thin membrane can be incubated at a temperature from room temperature to 50° C., for example, for 10 minutes to 30 hours so that a part of the thin membrane is allowed to be digested by a protease, and the thin membrane can be optionally stained with a dye, if necessary, and then traces of digestion on the thin membrane can be detected to measure protease activity.

As preferred embodiments of the method of the present invention, provided is the aforementioned method, wherein the biosample is isolated and collected from a mammal including a human, preferably a patient or a mammal suspected to have a disease, an experimental animal or the like. As the biosample, solid samples such as tissue pieces as well as non-solid samples such as samples containing cells or tissue fragment collected from tissues by suction, blood, lymph and saliva may be used. For example, a preferred embodiment of the present invention includes the aforementioned method wherein the biosample is a cancer tissue, lymph node, tissue of periodontal disease, gingival crevicular fluid, tissue or fluid contained in destructive morbid tissues (e.g., synovial fluid of rheumatic morbidity, exudate of alveolar pyorrhea tissue), pleural effusion, ascite, cerebrospinal fluid, mammary gland abnormal secretion fluid, ovarian cystic fluid, renal cystic fluid, pancreatic fluid, sputum, blood or blood cells. In the methods utilizing continuous slices, tissue slices may be used as the biosample.

The aforementioned method, wherein detection of a trace of digestion is performed by using a microscope or visual inspection; and the aforementioned method, wherein a trace of digestion is quantified or numerically represented by using an image processing system are preferred embodiments of the method of the present invention. Further, washing of the thin membrane is preferably performed with water, methanol, ethanol, a solution of a surfactant, an aqueous solution of glycerin, an aqueous solution of polyethylene glycol or a mixture thereof.

BEST MODE FOR CARRYING OUT THE INVENTION

The numerical ranges represented by "(from)-to-" in the specification are ranges including numerical values of their lower limits and upper limits. The term "measurement" used in the specification should be construed in its broadest sense including qualitative and quantitative measurements. In the method for measuring protease activity according to the present invention, a protease substrate (one or more kinds of substances selected from the group consisting of transferrin derivatives and albumin derivatives) in the thin membrane is digested by a protease contained in the sample, and traces of digestion are formed on the thin membrane. In the specification, "digestion" means enzymatic degradation of a substance selected from the group consisting of transferrin derivatives and albumin derivatives by a protease.

Then, by staining the thin membrane, for example, the traces of digestion can be detected under a microscope as portions showing a low optical density, and thus presence of protease activity in the sample can be detected. The substrate and the colorant in the digested portions are washed down by washing of the thin membrane, and this procedure makes detection of the traces of digestion easier. For the washing, water, methanol, ethanol, a solution of a surfactant, an aqueous solution of glycerin, an aqueous solution of polyethylene glycol, or a mixture thereof can be used. When a thin membrane containing a colorant is used, washing is preferably performed for the detection of traces of digestion.

Examples of the proteases that can be an object of the present invention include matrix metalloproteinases, serine proteases, and cysteine proteases. These enzymes are explained in detail in "Gan Ten'i No Bunshi Kiko (Molecular Mechanism of Cancer Metastasis)", Ed. By T. Tsuruo, pp.92–107, Medical View Co., Ltd., 1993. Among them, MMP-7 is the most suitable measurement object for the method of the present invention.

A thin membrane comprising a transferrin derivative or albumin derivative is hardly digested by MMP-2, MMP-3, or MMP-9, and accordingly, such a membrane is suitable for measurement in which higher selectivity for MMP-7 is required. Further, the measurement can be performed for, besides MMP-7, serine proteases and cysteine proteases such as cathepsin D and trypsin, as objective proteases.

As transferrins used in the present invention, transferrins derived from human, bovine, swine or other animals, or those having an amino acid sequence homologous thereto and produced by using genetic engineering techniques can be preferably used. Both of holo-type and apo-type transferrins can be preferably used. As the transferrin derivatives, those obtained by oxidation of the disulfide bond with performic acid, S-sulfocysteine derivatives obtained by sulfitolysis of the disulfide bond, those obtained by cleavage of the disulfide bond with a reducing agent and then S-alkylation with an alkylating agent and the like can be preferably used. As the alkylating agent, iodoacetic acid and iodoacetic acid amide, as well as the compounds mentioned below can be preferably used: acetic acid 2-bromoethyl ester, (S)-(+)-2-amino-4-bromobutyryl hydrobromide, bromoacetaldehyde diethyl acetal, 2-bromoacetamide, bromoacetic acid t-butyl ester, bromoacetic acid methyl ester, bromoacetonitrile, allyl bromide, 2,2-bis(bromomethyl)-1,3-propanediol, bromoacetaldehyde dimethyl acetal, bromoacetic acid, bromoacetic acid ethyl ester, bromoacetone, 4-(bromoacetylamino)benzoic acid, 4-(bromoacetyl)morpholine, 4-bromo-2-butanesulfonic acid sodium salt, 4-bromo-1-butanol, 4-bromo-1-butene, 2-bromo-N-tert-butyl-3,3-dimethylbutylamide, 4-bromo-n-butyric acid, 3-bromobutyronitrile, 3-bromo-2-(bromomethyl)propionic acid, 1-bromo-2-butanol, 1-bromo-2-butanone, 4-bromobutyl acetate, 2-bromo-n-butyric acid, a-bromo-γ-butyrolactone, 4-bromobutyronitrile, ((1R)-(endo, anti))-(+)-3-bromocamphor-8-sulfonic acid ammonium salt, (1S)-(+)-3-bromocamphor-10-sulfonic acid hydrate, 2-bromo-2-cyano-N,N-dimethylacetamide, 2-bromoethanesulfonic acid sodium salt, 2-bromoethylamine hydrobromide, 4-(2-bromoethyl)benzoic acid, 2-bromoethyl methyl ester, (+)-3-bromocamphor-8-sulfonic acid ammonium salt, bromocholine bromide, 1-bromo-2,2-dimethoxypropane, 2-bromoethanol, 4-(2-bromoethyl)benzenesulfonic acid, 2-(2-bromoethyl)-1,3-dioxane, 2-bromoethylphosphonic acid diethyl ester, 2-bromoisobutyric acid, 2-bromomalonamide, 2-(bromomethyl)acrylic acid, 2-bromomethyl-1,3-dioxolane, 2-(bromomethyl)-2-(hydroxymethyl)-1,3-propanediol, bromonitromethane, a-bromophenylacetic acid, 2-bromoisovaleric acid, bromomalonic acid diethyl ester, 4-(bromomethyl)benzoic acid, 5-bromo-1-methylhydantoin, 4-bromomethylphenylacetic acid, 2-bromo-2-nitro-1,3-propanediol, 3-bromo-1,2-propanediol, 3-bromopropanesulfonic acid, 1-bromo-2-propanol, 3-bromopropionaldehyde diethyl acetal, 2-bromopropionamide, 2-bromopropionic acid, 2-bromopropionitrile, 3-bromopropylamine hydrobromide, 3-bromopropanesulfonic acid sodium salt, 3-bromo-1-propanol, 3-bromopropionaldehyde dimethyl acetal, 3-bromopropionamide, 3-bromopropionic acid, 3-bromopropionitrile, (3-bromopropyl) phosphonic acid, (3-bromopropyl)trimethylammonium bromide, 3-bromopyruvic acid hydrate, 2-bromo-1,1,1-triethoxypropane, 2-bromo-n-valeric acid, dibromoacetonitrile, epibromohydrin, N-methylsulfonyl-3-bromopropionamide, 3-bromopyruvic acid, bromosuccinic acid, 11-bromoundecanoic acid, bromovalerylurea, 2,3-dibromo-1-propanol, ethyl bromopyruvate, tetrahydrofurfuryl bromide, N-(3-carboxyethyl)maleamidic acid, cis-aconitic acid, acrylic acid 2-carboxyethyl ester, fumaric acid monoethyl ester, maleic acid, maleic acid monoamide, maleic acid monomethyl ester, N-(3-carboxypropyl)maleamidic acid, acrylic acid, acrylonitrile, 2-(acryloylamino)isobutyric acid, itaconic acid, maleic acid disodium salt, maleic acid monoethyl ester, N-methyl-(maleic acid monoamide), 2-acrylamido-2-methylpropanesulfonic acid, 2-aminoethyl hydrogensulfate, (2-bromoethyl)methyl sulfate, 1,4-butanesultone, 1,2:5,6-di-O-isopropylidene-3-O-(methylsulfonyl)-α-D-glucofuranose, 2,2-dimethyl-1,3-dioxolan-4-ylmethyl p-toluenesulfonate, methacrylic acid 3-sulfopropyl ester potassium salt, (2-(acryloxy)ethyl)trimethylammonium methylsulfate, benzenesulfonic acid 2-methoxyethyl ester, 1,3-butanediol cyclic sulfate, cyanomethyl benzenesulfonate, dimethyl (4S,5S)-1,3,2-dioxathiolane-4,5-dicarboxylate 2,2-dioxide, 1,3,2-dioxathiolane 2,2-dioxide, (2-(methacryloyloxy)ethyl) trimethylammonium methylsulfate, N-(2-iodoethyl)-trifluoroacetamide, iodomethane, 2-iodoacetamide, iodoacetonitrile, 2-iodoethanol, 3-iodopropionic acid, sodium iodoacetate, iodoacetic acid, 4-iodobutyric acid, 3-iodopropanesulfonic acid sodium salt, lithium iodoacetate, methanesulfonic acid ethoxycarbonylmethyl ester, 2-methylpropane sultone, 1,3-propanediol cyclic sulfate, propargyl benzenesulfonate, tetraethylene glycol monooctyl ether methanesulfonate, p-toluenesulfonic acid pentafluorobenzyl ester, p-toluenesulfonic acid 2-(2-n-propoxyethoxy)ethyl ester, methanesulfonic acid 2-methoxyethyl ester, methylpropane sultone, propane sultone, 3-sulfopropyl acrylate potassium salt, p-toluenesulfonic acid 2-ethoxyethyl ester, p-toluenesulfonic acid propargyl ester, 2-(p-toluenesulfonyl) ethanol, 5'-tosyladenosine, aziridine-2-carboxylic acid methyl ester, ethyleneimine, propyleneimine, 1-(2-hydroxyethyl)ethyleneimine, 4-vinylpyridine, vinylsulfonic acid sodium salt, monoethyl fumarate potassium salt, propiolic acid, trans, trans-muconic acid, maleimide, N-methylmaleimide, N-ethylmaleimide, N-hydroxymaleimide, N-carbamoylmaleimide and 3-maleimidopropionic acid.

As methods for producing transferrin derivatives, applicable methods include, for example, the methods described in "Shin Seikagaku Jikken Koza (Lecture of Biochemical Experiments, New Edition)" Vol. 1, Protein II, Primary Structure, pp.75–80, "Shin Seikagaku Jikken Koza (Lecture of Biochemical Experiments, New Edition)" Vol. 3, Saccharide II, Proteoglycan and Glucosaminoglycan, pp.249–250, and Methods in Enzymology, Vol. 11 (1967), pp.199–255, 315–317 and 541–548. As an example, a typical method of producing carboxymethyltransferrin based on reduction carboxymethylation will be explained below. Transferrin is first dissolved in 0.5 M Tris-hydrochloric acid buffer (pH 8.5) containing 7 M guanidine hydrochloride and 10 mM EDTA and the solution is adjusted to pH 8.3 or higher. After nitrogen gas substitution, dithiothreitol is added to reduce the disulfide bonds of the transferrin. Iodoacetic acid is added to allow reaction under light shielding to perform S-alkylation. Then, desalting is performed by dialysis or gel filtration to obtain a target substance. Each derivative can be obtained by using other S-alkylating agent instead of the iodoacetic acid. For the performic acid oxidation method and the sulfitolysis method, the methods described in the aforementioned "Shin Seikagaku Jikken Koza (Lecture of Biochemical Experiments, New Edition)" Vol. 1, Protein II, Primary Structure, p.76 can be used.

As albumin raw materials for producing albumin derivatives, albumins and conalbumins derived from human, bovine, swine, chicken, rabbit, rat, guinea pig, mouse, equine or other animals or those having an amino acid sequence homologous thereto and produced by using genetic engineering techniques can be preferably used. As the albumin derivatives, those obtained by oxidation of the disulfide bond with performic acid, S-sulfocysteine derivatives obtained by sulfitolysis of disulfides, those obtained by cleavage of disulfides with a reducing agent and then S-alkylation with an alkylating agent and the like can be preferably used. Non-derivatized albumin is hardly degraded by a matrix metalloproteinase, and therefore it is not preferred as a protease substrate. As alkylating agents for producing albumin derivatives, iodoacetic acid and iodoacetic acid amide, as well as the compounds specifically mentioned above as the alkylating agents for transferrin can be preferably used.

As methods for producing albumin derivatives, applicable methods include, for example, the methods described in "Shin Seikagaku Jikken Koza (Lecture of Biochemical Experiments, New Edition)" Vol. 1, Protein II, Primary Structure, pp.75–80, "Shin Seikagaku Jikken Koza (Lecture of Biochemical Experiments, New Edition)" Vol. 3, Saccharide II, Proteoglycan and Glucosaminoglycan, pp.249–250, Methods in Enzymology, Vol. 11 (1967), pp.199–255, 315–317 and 541–548. As an example, a typical method of producing carboxymethylated bovine serum albumin based on reduction carboxymethylation will be shown below. Bovine serum albumin is dissolved in 0.5 M Tris-hydrochloric acid buffer (pH 8.5) containing 7 M guanidine hydrochloride and 10 mM EDTA and the solution is adjusted to pH 8.3 or higher. After nitrogen gas substitution, dithiothreitol is added to reduce the disulfide bonds of the albumin. Iodoacetic acid is added to allow the reaction under light shielding to perform S-alkylation. Then, desalting can be performed by dialysis or gel filtration to obtain a target substance. Each derivative can be obtained by using other S-alkylating agent instead of the iodoacetic acid. For the performic acid oxidation method and the sulfitolysis method, the methods described in the aforementioned "Shin Seikagaku Jikken Koza (Lecture of Biochemical Experiments, New Edition)" Vol. 1, Protein II, Primary Structure, p.76 can be used.

The thin membrane of the present invention is formed on a support. The membrane is preferably formed on a flat support or a bottom surface of a container such as a 96-well plate as a support. Material and shape of the support are not particularly limited. However, when surface change of the thin membrane is observed under a microscope, or when the surface change is detected by spectrometric means such as absorption spectrophotometry and fluorometry, for example, the thin membrane is preferably formed on a flat transparent or translucent support. Examples of such a transparent or translucent polymer support include, for example, transparent or translucent plastic films made of polyethylene terephthalate, polyethylene naphthalate, atactic polystyrene, syndiotactic polystyrene, polycarbonate, triacetylcellulose, polymethyl methacrylate, polysulfone, polyarylate, polyethylen and the like. Paper sheets laminated with such plastics may also be used. Particularly preferred examples include polyethylene terephthalate, syndiotactic polystyrene and polyarylate, and a most preferred example includes polyethylene terephthalate. A support to be used, per se, may be colored.

A thickness of the support is not particularly limited. The thickness is preferably from 50 to 300 µm, more preferably from 100 to 200 µm, when a flat support in the shape of film is used. Most preferably, a support having a thickness of about 175 µm may be used. The thin membrane on the support can be formed in a monolayer or multilayer structure. The thin membrane should be prepared so as to have a surface as uniform as possible. For example, the thin membrane may preferably be formed so as to have a thickness of from about 0.5 to 10 µm, more preferably from about 0.5 to 7 µm, after drying.

For the preparation of the thin membrane, for example, given amounts of a protease inhibitor and a hardening agent as required and further a colorant solution or dispersion as required can be added to an aqueous solution of a protease substrate selected from the group consisting of transferrin derivatives and albumin derivatives and mixed uniformly, and the resulting solution or dispersion can be applied to a surface of a support and dried. Other protease substrates such as collagen, gelatin, proteoglycan, fibronectin, laminin, elastin and casein may be added to the aforementioned solution or dispersion as required. As methods for coating, dip coating method, roller coating method, curtain coating method, extrusion coating method and the like can be employed. However, methods for preparing the thin membrane are not limited to these examples, and methods conventionally used for the preparation of thin membranes in the field of photographic films, for example, may be appropriately employed.

When a thin membrane is formed on a support, an undercoat layer may be provided between the thin membrane and the support in order to improve the adhesion of the thin membrane and the support. For example, the undercoat layer may be formed by using a polymer or a copolymer obtained by polymerization of one or more kinds of monomers selected from vinyl chloride, vinylidene chloride, butadiene, styrene, methacrylic acid, acrylic acid, itaconic acid, maleic anhydride and the like, or a polymer such as polyethyleneimine, epoxy resin, grafted gelatin, nitrocellulose and the like. When a polyester support is used, adhesion between the support and the thin membrane may sometimes be improved by subjecting the surface of the support to corona discharge treatment, ultraviolet irradiation or glow discharge treatment instead of providing the undercoat layer. By subjecting the support to corona discharge treatment, ultraviolet irradiation or glow discharge treatment and then applying an undercoat layer, the adhesion between the support and the thin membrane may also be improved.

The wording "a thin membrane formed on a support" and synonyms thereof used in the present specification should not be construed to exclude those having one or more undercoat layers and/or those of which support is subjected to a surface treatment. However, means for improving the adhesion of the thin membrane and the support is not limited to those mentioned above, and for example, those conventionally used in the field of photographic films and other fields can be appropriately used. When the thin membrane is formed by laminating a plurality of layers, an intermediate layer can further be provided between two laminated layers. The term "laminated" used in the present specification should not be construed so as to limit lamination two layers in direct contact. Means for appropriately providing such an intermediate layer are generally used, for example, in the field of photographic films and the like. It is also preferable to provide a protective layer on a membrane formed on a support surface, and such a protective layer is commonly used in the field of photographic films and the like.

Besides a protease substrate selected from the group consisting of transferrin derivatives and albumin derivatives and a hardening agent as required, a colorant and/or a protease inhibitor can be further added to the thin membrane as required. In addition, other various kinds of additives may be added to the thin membrane as required. Examples of the additives include surface active agents for facilitating application of the thin membrane, plasticizers for improving membrane quality (e.g., glycerin), oils or emulsifiers for dispersing the colorant, preservatives, fungicides, acids or bases for controlling pH, inorganic ions such as $Ca^{++}$ for controlling enzymatic activity and the like. However, the additives are not limited to these examples. Antistatic means may also be provided for the thin membrane of the present invention. For example, those showing a surface resistivity of $10^{12}$ Ω or less for the protease substrate layer side or the opposite side can be preferably used. As means for reducing surface resistivity of the membrane, for example, the methods described in Japanese Patent Application No. 2000-24011 can be used, or techniques used for photographic films can be used.

For the manufacture of the thin membrane of the present invention, for example, the following additives can be used as required: hardening agents (Research Disclosure (RD) 17643, page 26; RD 18716, page 651, left column; RD 307105, pages 874–875), binders (RD 17643, page 26; RD 18716, page 651, left column; RD 307105, pages 873–874), plasticizers or lubricants (RD 17643, page 27; RD 18716, page 650, right column; RD 307105, page 876), application aids or surface active agents (RD 17643, pages 26–27; RD 18716, page 650, right column; RD 307105, pages 875–876), antistatic agents (RD 17643, page 27; RD 18716, page 650, right column; RD 307105, pages 876–877), and matting agents (RD 307105, pages 878–879). All of these additives are widely used in the field of photographic films, and can be similarly used for the manufacture of the thin membrane of the present invention.

For the manufacture of the thin membrane of the present invention, an organic or inorganic hardening agent can be used as required. The hardening agent may be suitably selected from, for example, that can be used for accelerating curing of gelatin. The hardening agent should be chosen so as not to affect activity of a protease as an object of the measurement. For example, active halogen compounds (2,4-dichloro-6-hydroxy-1,3,5-triazine and sodium salt thereof and the like) and active vinyl compounds (1,3-bisvinylsulfonyl-2-propanol, 1,2-bis(vinylsulfonylacetamido)ethane, bis(vinylsulfonylmethyl) ether, vinyl polymers having vinylsulfonyl groups on the side chains and the like) may be used, and 1,2-bis(vinylsulfonylacetamido)-ethane may preferably be used.

As the protease inhibitor used for the present invention, various chelating agents may be used which are known to inhibit matrix metalloproteinases, especially EDTA or o-phenanthroline. Inhibitors including tissue inhibitors of metalloproteinase (TIMP), Batimastat, Marimastat, CGS27023A and the like can be used as matrix protease-specific inhibitors, and these inhibitors are described in, for example, "Saibo Kogaku (Cell Engineering)", Vol. 17, p.561 (1998). Furthermore, as serine protease inhibitors, inhibitors including phenylmethanesulfonyl fluoride, plasminogen activator inhibitor 1, gabexate mesilate, aprotinin, leupeptin and the like can be used, and some of these are described in, for example, "Protease To Seitai Kino (Protease and Biological Functions Thereof)" in Gendai Kagaku (Current Chemistry), Special edition, Vol. 22, p.224 (1993). However, the protease inhibitor are not limited to these compounds.

When a colorant is added to the thin membrane of the present invention, it becomes possible to detect traces of digestion formed on the thin membrane by an action of protease after washing of the thin membrane with water. The colorants are not particularly limited so long as they have absorption in a visible region, and various colorants including known substances can be used. As the colorant, either a fluorescent colorant or a colorant other than fluorescent colorant may be used. When a polymer support is used, it is preferable to use a colorant other than fluorescent colorant. One kind of colorant may be used, or two or more kinds of colorants may be used in combination. As the colorant, either a dye or pigment may be used, or the both may be used in combination. For example, when a laminated thin membrane is used, each layer may contain a colorant of different color.

Although amount of colorant added to the thin membrane is not particularly limited, the amount is generally from 0.001 to 10 mmol/m$^2$, preferably from 0.01 to 1 mmol/m$^2$, as a total amount of a colorant for unit area of the thin membrane. Types of colorants and methods for adding the colorants into the thin membrane, which can be suitably used for the manufacture of the thin membrane, are described in Japanese Patent Application No. 11-365074/1999. When a fluorescent colorant is used, a fluorescent colorant that emits fluorescence in visible region or near-infrared region or the like may also be used, as well as fluorescent colorants such as fluorescein and rhodamine. However, type of the fluorescent colorant is not particularly limited. Further, a colorant or fluorescent colorant having a property of reacting with a transferrin derivative or albumin derivative to bind thereto may also be used. Typical examples of such a substance include, but not limited thereto, active orange GT, fluorescein isothiocyanate and the like.

Examples of the dye include, for example, azo dyes, azomethine dyes, indoaniline dyes, benzoquinone dyes, naphtoquinone dyes, anthraquinone dyes, diphenylmethane dyes, triphenylmethane dyes, xanthene dyes, acridine dyes, azine dyes, oxazine dyes, thiazine dyes, oxonol dyes, melocyanine dyes, cyanine dyes, arylidene dyes, stilyl dyes, phthalocyanine dyes, perinone dyes, indigo dyes, thioindigo dyes, quinoline dyes, nitro dyes, nitroso dyes and the like. Specific compounds are described in "Shinban Senryo Binran (Dye Handbook, New Edition)", edited by The Society of Synthetic Organic Chemistry, Japan, Maruzen, 1970); "Color Index", The Society of Dyers and Colourists; "Shikizai Kogaku Handbook (Color Material Engineering Handbook)", edited by Japan Society of Color Material, Asakura Shoten, 1989 and the like. Although a water-soluble dye can also be used for the production of the thin membrane of the present invention, an oil-soluble dye is preferred since it does not adversely affect an enzymatic reaction. Specific examples of preferred dyes that can be added to the thin membrane are described in Japanese Patent Application No. 11-365074/1999. However, the dye is not limited to those dyes.

The kind of the pigment used for the present invention is not particularly limited, and either an organic pigment or an inorganic pigment may be used. Further, as the pigment, known pigments disclosed in a number of references and novel compounds may be used, as well as commercially available pigments. Specifically, examples of the organic pigments include, for example, azo pigments (azo lake pigments, insoluble monoazo pigments, insoluble dis-azo pigments, condensed azo pigments, metal complex azo pigments, chelate azo pigments), polycyclic pigments (such as phthalocyanine pigments, anthraquinone pigments, perylene and perinone pigments, indigo pigments, thioindigo pigments, quinacridone pigments, dioxazine pigments, isoindolinone pigments, quinophthalone pigments diketopyrrolopyrrole pigments), dyeing lake pigments (lake pigments of acidic or basic dyes) and azine pigments as well as other pigments (such as nitroso pigments, alizarin lake pigments, alkali blue) and the like. Examples of the inorganic pigments include ultramarine, cobalt blue and the like.

Among them, oil-soluble pigments are preferred since they do not adversely affect the enzymatic reaction. In order to obtain preferred bluish color tone, preferred examples include phthalocyanine pigments, indanthrone pigments of anthraquinone type, triarylcarbonium pigments of dyeing lake pigment type, indigo, as well as ultramarine blue and cobalt blue, which are inorganic pigments. In order to further control a color tone, a red or purple pigment, for example, dioxazine pigments, quinacridone pigments and diketopyrrolopyrrole pigments, may be used in combination with the aforementioned blue pigments. As for pigments, "Color Index", edited by The Society of Dyers and Colourists; "Kaitei Sinban Ganryo Binran (Pigment Handbook, Revised New Edition)", edited by Japan Pigment Technology Association, 1989; "Shin-Ganryo Oyo Gijutsu ("Newest Pigment Applied Technology", CMC Shuppan, 1986; "Insatsu Ink Gijutsu (Printing Ink Technology)", CMC Shuppan, 1984;

W. Herbst and K. Hunger, Industrial Organic Pigments, VCH Verlagsgesellschaft, 1993 and the like can be referred to.

Preferred examples of the blue pigments include C.I. Pigment Blue 15, 15:1, 15:2, 15:3, 15:4 and 15:6 (copper phthalocyanine) of phthalocyanine type, monochloro- or low chlorinated copper phthalocyanine, C.I. Pigment Blue 16 (non-metal phthalocyanine), phthalocyanines having Zn, Al or Ti as the center metal, C.I. Pigment Blues 60 and halogen-substituted derivatives thereof of indanthrone type, which are also known as vat dyes, for example, C.I. Pigment Blue 64 and 21, C.I. Pigment Blue 25 of azo type, C.I. Pigment Blue 66 of indigo type, C.I. Pigment Blue 63, which is a lake pigment, C.I. Pigment Blue 1, 2, 3, 9, 10, 14, 18, 19, 24:1, 24:x, 56, 61 and 62, which are lake pigments of triarylcarbonium type acid dyes or base dyes, and the like.

Preferred examples of the red and purple pigments include C.I. Pigment Violet 23 and 37 of dioxazine type, C.I. Pigment Violet 13, 25, 32, 44, 50, C.I. Pigment Red 23, 52:1, 57:1, 63:2, 146, 150, 151, 175, 176, 185, 187 and 245 of azo type, C.I. Pigment Violet 19, 42, C.I. Pigment Red 122, 192, 202, 207 and 209 of quinacridone type, C.I. Pigment Violet 1, 2, 3, 27, 39, C.I. Pigment Red 81:1, which are lake pigments of triarylcarbonium type, C.I. Pigment Violet 29 of perylene type, C.I. Pigment Violet 5:1, 31 and 33 of anthraquinone type, C.I. Pigment Red 38 and 88 of thioindigo type and the like.

Although the aforementioned pigments, per se, may be used for the manufacture of the thin membrane of the present invention, pigments subjected to a surface treatment may also be used. Examples of methods for the surface treatment include, for example, methods of surface coating with a resin or wax, methods of adhering a surface active agent, methods of binding a reactive substance (for example, silane coupling agents, epoxy compounds, polyisocyanates etc.) to pigment surfaces and the like, and specific means for the surface treatment are described in "Kinzoku Sekken No Seishitsu To Oyo (Properties and Applications of Metal Soap)", Saiwai Shobo; "Insatsu Ink Gijutsu (Technology of Printing Ink)", CMC Shuppan, 1984; "Saishin Ganryo Oyo Gijutsu (Newest Pigment Applied Technology)", CMC Shuppan, 1986 and the like.

For the manufacture of the thin membrane, it is generally desirable to disperse a pigment in the protease substrate, and a dispersing agent can be used for this purpose. The kind of the dispersing agent is not particularly limited, and various dispersing agents can be used depending on the combination of the protease substrate and the pigment to be used. For example, surfactant-type low molecule dispersing agents, macromolecule-type dispersing agents and the like may be used. When the dispersing agent is used in a hydrophobic protease substrate, it is preferred to use a macromolecule-type dispersing agent from a standpoint of dispersion stability. Examples of the dispersing agent include those disclosed in Japanese Patent Unexamined Publication No. 3-69949/1991, EP-A-549486 and the like.

The particle size of the pigment used for the manufacture of the thin membrane of the present invention is, for example, preferably in the range of 0.01–10 μm, more preferably in the range of fom 0.05 to 1 μm, after dispersion. As the methods for dispersing the pigment in the protease substrate, known dispersion techniques used for the manufacture of inks or toners can be used. Examples of dispersing machines include, for example, sand mill, attriter, pearl mill, super mill, ball mill, impeller, disperser, KD mill, colloid mill, dynatron, three-roll mill, pressurized kneader and the like, and details of the techniques are described in "Saishin Ganryo Oyo Gijutsu (Newest Pigment Applied Technology) ", CMC Shuppan, 1986.

In the thin membrane, a dye can be added as solid microparticle dispersion. Such a solid microparticle dispersion of a dye can be prepared by using a dispersing machine such as a ball mill, vibration ball mill, planetary ball mill, sand mill, colloid mill, jet mill and roller mill, and using a suitable solvent (such as water and alcohol) as required. The dispersion is preferably prepared by using a vertical or horizontal-type medium dispersing machine. The dispersion can also be obtained by a method comprising dissolving a dye in a suitable solvent and adding the solution to a poor solvent for the dye to cause deposition of the dye as microcrystals, a method comprising first dissolving a dye by controlling pH, and then changing pH to cause deposition of the dye as microcrystals and the like. In any case, it is preferable to use a dispersing agent.

A thin membrane containing solid microparticle dispersion of a dye can be formed by dispersing solid microparticles of a dye obtained as described above in a suitable protease substrate to prepare a substantially homogenous solid microparticle dispersion and applying this dispersion on a desired support. Further, another employable method comprises applying a dye in a dissociated state in the form of salt as an aqueous solution and coating acidic gelatin thereon to simultaneously obtain deposition and dispersion. As the dispersing agent, for example, known anionic, cationic, nonionic or amphoteric low molecule or macromolecule dispersing agents can be used. Examples include the dispersing agents disclosed in Japanese Patent Unexamined Publication No. 52-92716/1977, International Patent Publication WO88/04794, and Japanese Patent Unexamined Publication No. 10-20496/1998. It is particularly preferable to use an anionic and/or nonionic-type macromolecule dispersing agent.

The colorant contained in the thin membrane of the present invention may be used in combination with ultraviolet absorbers disclosed in Japanese Patent Unexamined Publication Nos. 62-215272/1987 (page 125, upper right column, line 2 to page 127, lower left column, last line), 2-33144/1990 (page 37, lower right column, line 14 to page 38, upper left column, line 11), EP0.355.600A2 (page 85, lines 22–31), and anti-fading agents disclosed in Japanese Patent Unexamined Publication No. 07-104448/1995 (column 70, line 10 to column 71, line 2).

The colorant can be introduced into the thin membrane by various known dispersion methods such as the methods disclosed in Japanese Patent Unexamined Publication No. 07-104448/1995 (column 71, line 3 to column 72, line 11) and the like. The oil-in-water dispersion method may also be employed, in which a colorant is dissolved in an organic solvent having a high boiling point (an organic solvent having a low boiling point may be used in combination, as required), then emulsion-dispersed in an aqueous solution of a protease substrate such as gelatin. Examples of the organic solvent having a high boiling point used for the oil-in-water dispersion method are described in U.S. Pat. No. 2,322,027 and the like. Further, the latex dispersion method as one of the polymer dispersion methods and examples of latex are disclosed in U.S. Pat. No. 4,199,363, West German Patent Application (OLS) Nos. 2,541,274 and 2,541,230, Japanese Patent Publication No. 53-41091/1988, European Patent Publication No. 029104 and the like, and they can be used for the manufacture of the thin membrane. The dispersion method using an organic solvent-soluble polymer is disclosed in International Patent Publication WO88/00723.

Examples of the organic solvent having a high boiling point that can be used for the oil-in-water dispersion method include, for example, phthalic acid esters (for example, dibutyl phthalate, dioctyl phthalate, dicyclohexyl phthalate, di-2-ethylhexyl phthalate, decyl phthalate, bis(2,4-di-tert-amylphenyl) isophthalate, bis(1,1-diethylpropyl) phthalate), esters of phosphoric acid or phosphonic acid (for example, diphenyl phosphate, triphenyl phosphate, tricresyl phosphate, 2-ethylhexyl diphenyl phosphate, dioctyl butyl phosphate, tricyclohexyl phosphate, tri-2-ethylhexyl phosphate, tridodecyl phosphate, di-2-ethylhexyl phenyl phosphate), benzoic acid esters (for example, 2-ethylhexyl benzoate, 2,4-dichlorobenzoate, dodecyl benzoate, 2-ethylhexyl p-hydroxybenzoate), amides (for example, N,N-diethyl-dodecaneamide, N,N-diethyl-laurylamide), alcohols or phenols (such as isostearyl alcohol, 2,4-di-tert-amylphenol), aliphatic esters (for example, dibutoxyethyl succinate, di-2-ethylhexyl succinate, 2-hexyldecyl tetradecanoate, tributyl citrate, diethyl azelate, isostearyl lactate, trioctyl citrate), aniline derivatives (such as N,N-dibutyl-2-butoxy-5-tert-octylaniline), chlorinated paraffins (paraffins having a chlorine content of 10–80%), trimesic acid esters (for example, tributyl trimesicate), dodecylbenzene, diisopropylnaphthalene, phenols (for example, 2,4-di-tert-amylphenol, 4-dodecyloxyphenol, 4-dodecyloxycarbonylphenol, 4-(4-dodecyloxyphenylsulfonyl)phenol), carboxylic acids (for example, 2-(2,4-di-tert-amylphenoxybutyric acid, 2-ethoxyoctanedecanoic acid), alkylphosphoric acid (for example, di-2-(ethylhexyl)phosphoric acid, diphenylphosphoric acid) and the like. An organic solvent having a boiling point of from 30° C. to about 160° C. (for example, ethyl acetate, butyl acetate, ethyl propionate, methyl ethyl ketone, cyclohexanone, 2-ethoxyethyl acetate, dimethylformamide) may be used in combination as an auxiliary solvent.

The amount of the organic solvent having a high boiling point may be 10 g or less, preferably of 5 g or less, more preferably from 0.1 to 1 g, for 1 g of a colorant used. For 1 g of the protease substrate, the amount may suitably be 1 ml or less, preferably 0.5 ml or less, more preferably 0.3 ml or less. When a hydrophobic colorant is dispersed in hydrophilic colloids, various surface active agents can be used. For example, those mentioned in Japanese Patent Unexamined Publication No. 59-157636/1984, pages 37–38 and Research Disclosure (abbreviated as RD hereinafter in the specification) 17643 as surface active agents can be used.

As the sample used for the measurement of protease activity, a biosample can be preferably used. As the biosample, a biosample isolated and collected from a mammal including a human can be used. For example, a biosample isolated and collected from a mammal with a disease, mammal suspected to have a disease, experimental animal or the like can be used. The form of the biosample is not particularly limited, and solid samples such as tissue slices and non-solid samples such as body fluid can be used. Examples of the non-solid samples include samples containing cells or tissue fragments collected from tissues by suction, body fluids such as blood, lymph and saliva. There can be used, for example, cancer tissues isolated and collected from tumor tissues of lung cancer, stomach cancer, esophageal cancer, colon cancer, breast cancer, uterine cancer, ovarian cancer, thyroid cancer, liver cancer, intraoral cancer, prostatic cancer, renal cancer, bladder cancer and the like by surgical operation or histological examination, lymph nodes, tissues of periodontal diseases, tissues such as synovial membranes and bone tissues isolated and collected from tissues of rheumatoid arthritis patients by surgical operation or histological examination, gingival crevicular fluids, fluids contained in destructive morbid tissues (e.g., synovial fluid of rheumatic morbidity, exudate of alveolar pyorrhea tissue), pleural effusions, ascites, cerebrospinal fluids, mammary gland abnormal secretion fluids, ovarian cystic fluids, renal cystic fluids, sputum, blood, blood cells and the like.

When the sample is a tissue, for example, a slice having a thickness of 1 to 10 μm, preferably 4 to 6 μm, may be prepared from a sample rapidly frozen in liquid nitrogen by using an apparatus for preparing frozen sections, and then the slice may be applied to a thin membrane to bring the sample into contact with the thin membrane. A tissue specimen collected by paracentesis and suction may also be rapidly frozen with a molding material such as compounds and made into slices in a similar manner for use. When a non-solid sample containing cells or tissue fragments is used, which is collected from tissues by paracentesis and suction, the sucked sample may be discharged on a thin membrane so that the cells can adhere to the thin membrane in a dispersed state. It is also possible to adhere cells collected from a tissue by paracentesis and suction onto the thin membrane by using a cytospin apparatus. Further, when the biosample is a piece of tissue, moisture of the collected tissue may be wiped lightly, and then the tissue can be left standing on a thin membrane containing a protease substrate for from 1 to 30 minutes for the contact of the sample with the thin membrane.

When a non-solid sample such as synovial fluid collected from a patient with rheumatoid arthritis is used, the sample is diluted to an appropriate concentration and/or subjected to a necessary pretreatment, about 1 to 50 μl, preferably about 1 to 20 μl, of the sample can be dropped onto the thin membrane. When gingival crevicular fluid of periodontal disease is used as a sample, a method is employable wherein a piece of filter paper may be inserted into gingival crevice to collect about 5 to 10 μl of gingival crevicular fluid, and the filter paper may be applied to a thin membrane. After the collection of gingival crevicular fluid, the gingival crevicular fluid may be optionally extracted from the filter paper using distilled water or a suitable buffer (for example, 50 mM Tris-HCl, pH 7.5, 10 mM $CaCl_2$, 0.2 M NaCl), and the extract may be dropped onto a thin membrane, as required. When body fluid that can be collected in a larger amount (cystic fluid and the like) is used, a result with good reproducibility can be obtained by immersing a part of the thin membrane into a vessel containing the sample.

After a sample containing a protease is brought into contact with a thin membrane by adhering a tissue slice containing a protease substrate to the thin membrane, or dropping a liquid sample containing a protease substrate onto the thin membrane or the like, the thin membrane is incubated at a temperature suitable for expression of the protease activity, e.g., a temperature of from room temperature to 50° C., more preferably a temperature of from 37 to 47° C., under a saturated humid condition for a period required for digestion of the protease substrate selected from the group consisting of transferrin derivatives and albumin derivative, for example, about 10 minutes to 30 hours. Although the time required for the digestion may vary depending on the kinds of the sample and the thin membrane, the incubation is preferably performed at 37° C. for 10 minutes to 48 hours, more preferably 10 minutes to 24 hours, for a tissue slice or cells obtained by suction or non-solid sample containing tissue fragments, or for 10 minutes to 24 hours, preferably 10 minutes to 6 hours, for a liquid sample such as exudate, to allow formation of traces of digestion on the thin membrane by protease in the sample.

Then, the thin membrane is stained and/or washed to remove the digested protease substrate and a colorant contained in the digestion product when the thin membrane contains a colorant. Furthermore, when a method is additionally performed to stain cell nuclei contained in the biosample on the thin membrane with hematoxylin or Methyl Green, sites of traces of digestion can be accurately determined. Further, when a thin membrane that does not contain a colorant is used, the detection of traces of digestion becomes easy by staining the thin membrane after the thin membrane and a sample are brought into contact with each other. As the colorant used for the staining, Amido Black 10B, Ponceau 3R and Biebrich Scarlet, as well as various kinds of colorants described in Japanese Patent Application No. 11-192130/1999 can be used.

By adhering one of two or more substantially continuous slices of a biosample to a thin membrane not containing a protease inhibitor, and adhering another slice among the remaining slices to a thin membrane containing a protease inhibitor, and then by comparing traces of digestion formed in each of the thin membranes, the kind of the protease can be identified. The kind of the protease inhibitor is not particularly limited, and chelating agents, matrix metalloproteinase inhibitors, serine protease inhibitors and the like can be suitably used.

When a thin membrane consisting of a monolayer is used which contains a protease substrate and a colorant, optical density of the thin membrane is reduced as the thin membrane is digested by a protease contained in a sample. However, when a thin membrane containing a protease substrate consists of laminated applied layers and a dye of different color is added to each of the layers, the color hue of the thin membrane changes with optical density as the thin membrane is digested by a protease in a sample. If such a thin membrane is used, it is easy to visually determine the strength of the digestion.

By measuring protease activity contained in a biosample using the thin membrane of the present invention, the conditions of the living body from which the sample is derived, for example, metastasis of cancer, progress of rheumatism and the like, can be investigated. For determining the strength of digestion in traces of digestion, there can be employed any of methods such as a method of judging by visual inspection under an optical microscope, a method of observing three-dimensional from of the membrane by using a confocal optical microscope, a method of measuring optical density of traces of digestion with a spectrometer, a method of storing an image captured by an optical microscope in a computer using a digital camera or scanner and performing various numerical evaluation of the traces of digestion by image analysis techniques and the like. When image analysis is performed, various data processing methods can be used, and the kind thereof is not particularly limited. However, it is preferable to numerically evaluate the degree of digestion by using integration of areas of traces of digestion, or integration of densities and areas of traces of digestion.

Techniques concerning methods of measuring protease activity by using a thin membrane containing a protease substrate are described in, for example, Japanese Patent Unexamined Publication No. 9-832035/1997, Japanese Patent Application Nos. 11-174826/1999, 11-192130/1999, 11-365074/1999, 2000-24011 and the like. Therefore, the present invention may be sometimes enabled more easily by referring to these references as required. The disclosures of these references are incorporated into the present specification by reference. Further, the entire disclosures of Japanese Patent Application Nos. 2000-83176 and 2000-187061 are incorporated in the present specification by reference.

EXAMPLES

The present invention will be explained more specifically with reference to the following examples. However, the scope of the present invention is not limited to these examples.

Example 1

Preparation of Carboxymethyltransferrin 10 g of bovine serum transferrin was dissolved in 3 L of 0.5 M Tris-hydrochloric acid buffer (pH 8.5) containing 7 M guanidine hydrochloride and 10 mM EDTA disodium. After inside of the vessel was purged with nitrogen gas, the reaction mixture was added with 10 g of dithiothreitol. The reaction mixture was stirred at room temperature for 2 hours and then added with 25 g of iodoacetic acid weighed in a place not exposed to direct light. The reaction was allowed at room temperature for 30 minutes under light shielding. After completion of the reaction, the reaction mixture was desalted by dialysis using a dialysis membrane having a cutoff molecular weight of 7,000. When the resulting reaction product was examined by SDS polyacrylamide electrophoresis, transferrin as the reaction material gave a band of a molecular weight of about 82,000, whilst the reaction product gave a band of an increased molecular weight about 88,000.

Example 2

Preparation of Cyanoethyltransferrin 10 g of bovine serum transferrin was dissolved in 2 L of 8 M urea aqueous solution. The reaction mixture was adjusted to pH 8.0 with sodium hydroxide, and inside of the vessel was purged with nitrogen gas. Then, the reaction mixture was added with 10 g of dithiothreitol. The reaction mixture was stirred at room temperature for 2 hours and then added with 6.9 g of acrylonitrile. Then, the reaction was allowed at room temperature for 4 hours. After completion of the reaction, the reaction mixture was desalted by dialysis using a dialysis membrane having a cutoff molecular weight of 7,000. When the resulting reaction product was examined by SDS polyacrylamide electrophoresis, the product gave a band on the higher molecular weight side relative to transferrin as the reaction material.

Example 3

Preparation of Ethylsuccinimidotransferrin 10 g of bovine serum transferrin was dissolved in 2 L of 8 M urea aqueous solution. The reaction mixture was adjusted to pH 8.0 with sodium hydroxide, and inside of the vessel was purged with nitrogen gas. Then, the reaction mixture was added with 10 g of dithiothreitol. The reaction mixture was stirred at room temperature for 2 hours and then added with 19 g of N-ethylmaleimide. After the reaction was carried out at room temperature for 2 hours, the reaction mixture was desalted by dialysis using a dialysis membrane having a cutoff molecular weight of 7,000. When the resulting reaction product was examined by SDS polyacrylamide electrophoresis, the product gave a band on the higher molecular weight side relative to transferrin as the reaction material.

Example 4

Preparation of Thin Membrane of Transferrin Derivative (Preparation of Support)

A clear PET film having a thickness of 175 μm was subjected to a surface corona discharge treatment and used for preparation of a support applied with undercoats composed of the following compositions. Electric resistivity of the back face was measured as $1 \times 10^8$ Ω.

| 1. Front surface | |
| --- | --- |
| Gelatin | 0.3 g/m2 |
| Hardening agent (1) | 0.001 g/m$^2$ |
| 2. Back surface | |
| Gelatin | 0.05 g/m$^2$ |
| Aqueous dispersion of stannic oxide doped with antimony oxide | 0.04 g/m$^2$ |
| Methylcellulose | 0.01 g/m$^2$ |
| Matting agent (PMMA polymer particles having average diameter of 3 μm) | 0.005 g/m$^2$ |
| Hardening agent (2) | 0.002 g/m$^2$ |

Hardening agent (1)

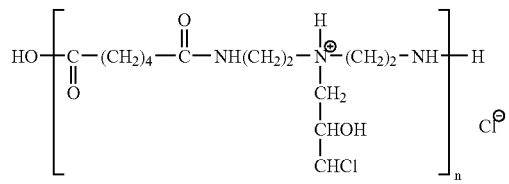

Hardening agent (2)

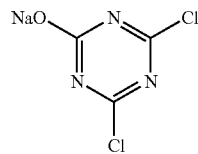

(Preparation of Coating Solution and Coating)

3 g of each of the transferrin derivatives obtained by the procedures of Examples 1 to 3 was dissolved in 100 mL of pure water, and pH was adjusted to from 7.0 to 7.5 with hydrochloric acid or NaOH. As a hardening agent, each 45 mg of 1,2-bis(vinylsulfonylacetamido)ethane was added. Each transferrin derivative solution was applied to the aforementioned support so as to give a membrane thickness of about 3 μm.

Example 5

Preparation of Transferrin Derivative Thin Membrane Containing Colorant

Thin membranes of transferrin derivatives containing a red colorant were prepared by using the same composition as that of Example 1 of Japanese Patent Application No. 11-365074/1999, except that the aforementioned transferrin derivatives were used instead of gelatin.

Example 6

Preparation of Carboxymethyltransferrin Thin Membrane Containing Chelating Agent 3 g of the carboxymethyltransferrin obtained by the procedure of Example 1 mentioned above was dissolved in 100 mL of pure water, and pH was adjusted to from 7.0 to 7.5 with hydrochloric acid or NaOH. 45 mg of 1,2-bis (vinylsulfonylacetamido)-ethane was added as a hardening agent, and 0.38 g of o-phenanthroline was added as a chelating agent. The transferrin derivative solution was applied to the support mentioned in Example 4 so as to give a membrane thickness of about 3 μm.

Example 7

Preparation of Carboxymethyltransferrin Thin Membrane Containing Colorant and Trypsin Inhibitor A thin membrane of carboxymethyltransferrin containing a red colorant and a trypsin inhibitor was prepared by using the same composition as that of Example 2 of Japanese Patent Application No. 11-365074/1999, except that carboxymethyltransferrin was used instead of gelatin, and 0.05 g of gabexate mesilate per 1 g of carboxymethyltransferrin was added instead of o-phenanthroline.

Example 8

Preparation of Gelatin Thin Membrane (Comparative Example)

10 g of acid-treated swine cutis gelatin was dissolved in 127 g of pure water and added with 150 mg of 1,2-bis (vinylsulfonylacetamido)ethane as a hardening agent. The solution was applied to the support mentioned in Example 4 so as to give a membrane thickness of about 3 μm.

Example 9

Digestion of Transferrin Thin Membrane and Gelatin Thin Membrane by Protease Solution (Protease Solution)
MMP-2 (2 u/mL, Yagai), MMP-3 (0.5 u/mL, Yagai) and MMP-7 (1 u/mL, Yagai) were each diluted 3 times with PBS, and MMP-9 (5 u/mL, Yagai) and bovine trypsin (Sigma) were each diluted to 1 u/mL with PBS.

(Preparation of Staining Solution)
In a volume of 75 ml of distilled water was added with 0.45 g of Biebrich Scarlet (Aldrich) and further added with 5 g of trichloroacetic acid and 75 ml of 100% ethanol, and then the dye was dissolved by stirring with a stirrer. Insoluble solids were removed by filtration through filter paper to prepare a staining solution.

(Experiment of Enzymatic Digestion of Membrane)
The aforementioned enzyme solutions were dropped onto the thin membranes of transferrin derivatives obtained in Example 4 and onto the gelatin thin membrane obtained in Example 8 in an amount of each 1 μl in an array, and incubated at 37° C. for 16 hours in a humid box. Then, the membranes were immersed in the Biebrich Scarlet staining solution for 4 minutes and washed with water for 10 minutes.

When the results were evaluated by visual inspection, the gelatin membrane was digested by all the enzymes, and holes were formed at the sites where the solutions were dropped. On the other hand, carboxymethyltransferrin, cyanoethyltransferrin and ethylsuccinimidotransferrin were scarcely digested by MMP-2, MMP-3 and MMP-9, but digested by MMP-7 like gelatin. Although these membranes were also digested by trypsin, the digestion was quite weaker as compared to that of the gelatin membrane. Based on these results, it was concluded that the selectivity for MMP-7 was increased in the thin membranes of transferrin derivatives.

Further, when a similar enzymatic digestion experiment was conducted for the thin membrane of carboxymethyltransferrin containing a chelating agent mentioned in Example 6, it was found that no digestion by MMP's occurred, but the membrane was digested only by trypsin. Furthermore, when the thin membrane of carboxymethyltransferrin containing a red colorant and trypsin inhibitor mentioned in Example 7 was dropped with the enzyme solutions, incubated at 37° C. for 16 hours in a humid box, washed with water and then observed, it was found that the membrane was apparently digested by MMP-7, but hardly digested by MMP-2, MMP-3, MMP-9 and trypsin.

Example 10

Measurement of Protease Activity of Esophageal Cancer Frozen Slice

An esophageal cancer specimen extracted by surgical operation was rapidly frozen, then sliced at −25° C. into slices having a thickness of 4 μm by using an apparatus for preparing frozen sections and adhered to the three kinds of transferring derivative thin membranes containing red colorant emulsion prepared according to Example 5 and the gelatin thin membrane. These membranes were incubated at 37° C. for 8 hours under 100% of relative humidity, air-dried and washed with water for 10 minutes. The membranes were immersed in a Mayer's hematoxylin solution for 2 minutes for nuclear staining, washed with water for 10 minutes, immersed in ethanol for 20 seconds for dehydration and then air-dried. Alternatively, the membranes were subjected to nuclear staining in a similar manner, washed with water for 10 minutes, immersed in 20% glycerin aqueous solution for 5 minutes and then air-dried. After the drying, a Cover Aid Film (Sakura Seiki Co., Ltd.) was adhered to each membrane by using xylene so as to cover the tissue slice for encapsulation of the esophageal cancer slice. When this film was held on a plastic mount and observed under an optical microscope, digestion of the thin membrane was observed for all of the thin membranes on each site contacting with the esophageal cancer tissue slice where the cancer cells were considered to be present based on the morphology of the nuclei, and thus presence of protease activity was verified. When the above process carried out with only modifications of steps of immersing the thin membrane in 20% glycerin aqueous solution and air-drying the membrane, similar results were obtained.

When the results of the carboxymethyltransferrin thin membrane and the gelatin thin membrane were compared, the gelatin thin membrane was digested in a broader area. Then, frozen slices were prepared from a peripheral portion of the extracted specimen, which was considered to be a normal tissue, and examined in a similar manner. As a result, almost no digestion was observed in the thin membranes of transferrin derivatives, whereas digestion was partly observed in the gelatin thin membrane. It was considered that the selectivity for cancer was increased in the thin membranes of transferrin derivatives, which was believed to be attributable to the increased selectivity for MMP-7 of the transferrin thin membranes as shown by the results of Example 9. Further, as a result of comparison of the thin membranes of the three kinds of transferrin derivatives, the carboxymethyltransferrin thin membrane gave the most favorable result with the best contrast between the digested portions and the portions not digested.

Example 11

Preparation of Carboxymethylated Bovine Serum Albumin 10 g of bovine serum albumin was dissolved in 3 L of 0.5 M Tris-hydrochloric acid buffer (pH 8.5) containing 7 M guanidine hydrochloride and 10 mM EDTA disodium. After inside of the vessel was purged with nitrogen gas, the reaction mixture was added with 10 g of dithiothreitol. The reaction mixture was stirred at room temperature for 2 hours and then added with 25 g of iodoacetic acid weighed in a place not exposed to direct light. The reaction was carried out at room temperature for 30 minutes under light shielding. After completion of the reaction, the reaction mixture was desalted by dialysis using a dialysis membrane having a cutoff molecular weight of 7,000. When the resulting reaction product was examined by SDS polyacrylamide electrophoresis, bovine serum albumin as the reaction material gave a band of a molecular weight of about 75,000, whilst the reaction product gave a band of an increased molecular weight of about 80,000.

Example 12

Preparation of Carboxymethylated Conalbumin 10 g of conalbumin was dissolved in 3 L of 0.5 M Tris-hydrochloric acid buffer (pH 8.5) containing 7 M urea and 10 mM EDTA disodium. After inside of the vessel was purged with nitrogen gas, the reaction mixture was added with 10 g of dithiothreitol. The reaction mixture was stirred at room temperature for 2 hours and then added with 25 g of iodoacetic acid weighed in a place not exposed to direct light. The reaction was carried out at room temperature for 30 minutes under light shielding. After completion of the reaction, the reaction mixture was desalted by dialysis using a dialysis membrane having a cutoff molecular weight of 7,000. When the resulting reaction product was examined by SDS polyacrylamide electrophoresis, conalbumin as the reaction material gave a band of a molecular weight of about 82,000, whilst the reaction product gave a band of an increased molecular weight of about 87,000.

Example 13

Preparation of Cyanoethylated Bovine Serum Albumin 10 g of bovine serum albumin was dissolved in 2 L of 8 M urea aqueous solution. The reaction mixture was adjusted to pH 8.0 with sodium hydroxide, and inside of the vessel was purged with nitrogen gas. Then, the reaction mixture was added with 10 g of dithiothreitol. The reaction mixture was stirred at room temperature for 2 hours and then added with 6.9 g of acrylonitrile. The reaction was carried out at room temperature for 4 hours. After completion of the reaction, the reaction mixture was desalted by dialysis using a dialysis membrane having a cutoff molecular weight of 7,000. When the resulting reaction product was examined by SDS polyacrylamide electrophoresis, the product gave a band on the higher molecular weight side relative to bovine serum albumin as the reaction raw material.

Example 14

Preparation of N-Ethylsuccinimidated Bovine Serum Albumin 10 g of bovine serum albumin was dissolved in 2 L of a 8 M urea aqueous solution. The reaction mixture was adjusted to pH 8.0, and inside of the vessel was purged with nitrogen gas. Then, the reaction mixture was added with 10 g of dithiothreitol. The reaction mixture was stirred at room temperature for 2 hours and then added with 19 g of N-ethylmaleimide. After the reaction was carried out at room temperature for 4 hours, the reaction mixture was desalted by dialysis using a dialysis membrane having a cutoff molecular weight of 7,000. When the resulting reaction product was examined by SDS polyacrylamide electrophoresis, the product gave a band on the higher molecular weight side relative to bovine serum albumin as the reaction raw material.

Example 15

Preparation of Thin Membrane of Albumin Derivative (Preparation of Support)

A clear PET film having a thickness of 175 μm was subjected to a surface corona discharge treatment and used for preparation of a support applied with undercoats composed of the following compositions. Electric resistivity of the back face was measured as $1 \times 10^8$ O.

| 1. Front surface | |
|---|---|
| Gelatin | 0.3 g/m² |
| Hardening agent (1) | 0.001 g/m² |
| 2. Back surface | |
| Gelatin | 0.05 g/m² |
| Aqueous dispersion of stannic oxide doped with antimony oxide | 0.04 g/m² |
| Methylcellulose | 0.01 g/m² |
| Matting agent (PMMA polymer particles having average diameter of 3 μm) | 0.005 g/m² |
| Hardening agent (2) | 0.002 g/m² |

Hardening agent (1)

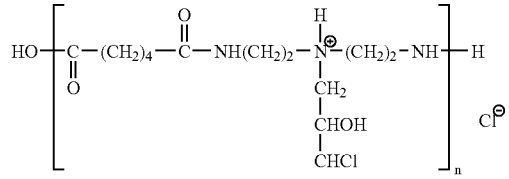

Hardening agent (2)

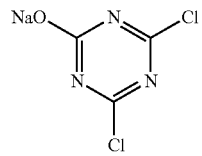

(Preparation of Coating Solution and Coating)

Each 3 g of the albumin derivatives obtained by the procedures of Examples 11 to 13 was dissolved in 100 mL of pure water, and pH was adjusted to from 7.0 to 7.5 with hydrochloric acid or NaOH. As a hardening agent, 45 mg for each of 1,2-bis(vinylsulfonylacetamido)ethane was added. Each albumin derivative solution was applied to the aforementioned support to give a membrane thickness of about 3 μm.

Example 16

Preparation of Albumin Derivative Thin Membrane Containing Colorant

Thin membranes of albumin derivatives containing a red colorant were prepared by using the same composition as that of Example 1 of Japanese Patent Application No. 11-365074/1999 except that the aforementioned albumin derivatives were used instead of gelatin. The thin membranes were stored at room temperature for 2 weeks after drying, then immersed in 100 mM calcium chloride aqueous solution for 10 minutes and air-dried.

Example 17

Preparation of Thin Membrane of Carboxymethylated Bovine Serum Albumin Containing Chelating Agent 3 g of the carboxymethylated bovine serum albumin obtained by the procedure of Example 11 mentioned above was dissolved in 100 mL of pure water, and pH was adjusted to from 7.0 to 7.5 with hydrochloric acid or NaOH. 45 mg of 1,2-bis(vinylsulfonylacetamido)ethane was added as a hardening agent, and 0.38 g of o-phenanthroline was added as a chelating agent. The albumin derivative solution was applied to the support mentioned in Example 15 to give a membrane thickness of about 3 μm.

Example 18

Preparation of Carboxymethylated Bovine Serum Albumin Thin Membrane Containing Colorant and Trypsin Inhibitor A thin membrane of carboxymethylated bovine serum albumin containing a red colorant and a trypsin inhibitor was prepared by using the same composition as that of Example 2 of Japanese Patent Application No. 11-365074/1999 except that carboxymethylated bovine serum albumin was used instead of gelatin, and 0.05 g of gabexate mesilate per 1 g of carboxymethylated bovine serum albumin was added instead of o-phenanthroline.

Example 19

Preparation of Gelatin Thin Membrane (Comparative Example)

10 g of acid-treated swine cutis gelatin was dissolved in 127 g of pure water and added with 150 mg of 1,2-bis (vinylsulfonylacetamido)ethane as a hardening agent. The solution was applied to the support mentioned in Example 15 to give a membrane thickness of about 3 μm.

Example 20

Digestion of Bovine Serum Albumin Derivative Thin Membrane and Gelatin Thin Membrane by Protease Solution (Protease Solution)

MMP-2 (2 u/mL, Yagai), MMP-3 (0.5 u/mL, Yagai) and MMP-7 (1 u/mL, Yagai) were each diluted 3 times with PBS, and MMP-9 (5 u/mL, Yagai) and bovine trypsin (Sigma) were each diluted to 1 u/mL with PBS.

(Preparation of Staining Solution)

75 ml of distilled water was added with 0.45 g of Biebrich Scarlet (Aldrich) and further added with 5 g of trichloroacetic acid and 75 ml of 100% ethanol. The dye was dissolved by stirring with a stirrer, and insoluble solids were removed by filtration through filter paper to prepare a staining solution.

(Experiment of Enzymatic Digestion of Membrane)

The aforementioned enzyme solutions were dropped each in an amount of 1 μl in an array onto the thin membranes of albumin derivatives obtained in Example 15 and the gelatin thin membrane obtained in Example 19, and then the membranes were incubated at 37° C. for 16 hours in a humid box. Then, the membranes were immersed in the Biebrich Scarlet staining solution for 4 minutes and washed with water for 10 minutes.

When the results were evaluated by visual inspection, the gelatin membrane was digested by all of the enzymes, and holes were formed at the sites where the solutions were dropped. On the other hand, carboxymethylated bovine serum albumin, cyanoethylated bovine serum albumin and N-ethylsuccinimidated bovine serum albumin were scarcely digested by MMP-2, MMP-3 and MMP-9, whist digested by MMP-7 like gelatin. These membranes were also digested by trypsin, however, the digestion was quite weaker compared with that of the gelatin membrane. From these results, it was concluded that the selectivity for MMP-7 was increased in the thin membranes of albumin derivatives.

Further, when a similar enzymatic digestion experiment was conducted for the thin membrane of carboxymethylated bovine serum albumin containing a chelating agent mentioned in Example 17, no digestion by MMPs occurred, whilst the membrane was digested only by trypsin. Furthermore, when the thin membrane of carboxymethylated bovine serum albumin containing a red colorant and trypsin inhibitor mentioned in Example 18 was dropped with the enzyme solutions, incubated at 37° C. for 16 hours in a humid box, and then washed with water and observed, it was found that the membrane was apparently digested by MMP-7, whilst was hardly digested by MMP-2, MMP-3, MMP-9 and trypsin.

Example 21

Measurement of Protease Activity of Esophageal Cancer Frozen Slice

An esophageal cancer specimen extracted by surgical operation was rapidly frozen, then sliced at −25° C. into slices having a thickness of 4 μm by using an apparatus for preparing frozen sections and adhered to each of the three kinds of albumin derivative thin membranes containing red colorant emulsion prepared in Example 16 and the gelatin thin membrane. These membranes were incubated at 37° C. for 8 hours under 100% of relative humidity, and then air-dried and washed with water for 10 minutes. The membranes were immersed in a Mayer's hematoxylin solution for 2 minutes for nuclear staining, washed with water for 10 minutes, immersed in ethanol for 20 seconds for dehydration and then air-dried. After the drying, a Cover Aid Film (Sakura Seiki Co., Ltd.) was adhered to each membrane by using xylene so as to cover the tissue slice for encapsulation of the esophageal cancer slice. When this film was held on a plastic mount and observed under an optical microscope, digestion of the thin membrane was observed for all of the thin membranes on each site contacting with the esophageal cancer tissue slice where the cancer cells were considered to be present based on the morphology of the nuclei, and thus presence of protease activity was verified.

When the results of the carboxymethylated bovine serum albumin thin membrane and the gelatin thin membrane were compared, the gelatin thin membrane gave a broader area of digestion. Then, frozen slices were prepared from a peripheral portion of the extracted specimen, which was considered to be a normal tissue, and examined in a similar manner. As a result, almost no digestion was observed in the thin membranes of albumin derivatives, whereas digestion was partly observed in the gelatin thin membrane. It was considered that the selectivity for cancer was increased in the thin membranes of albumin derivatives, which was considered to be attributable to the increased selectivity for MMP-7 of the albumin thin membranes as shown by the result of Example 20.

INDUSTRIAL APPLICABILITY

Traces of digestion are selectively formed by a particular class of protease on the thin membrane of the present invention. Accordingly, the membrane is useful for measurement of activity of the particular class of protease.

What is claimed is:

1. A thin membrane for measuring matrix metalloproteinase 7 (MMP-7) protease activity in a tissue slice or one or more cells, the membrane being formed on a support, and comprising at least one substance selected from the group consisting of a transferrin derivative and an albumin derivative, wherein said substance is crosslinked and/or substantially water-insoluble;
   wherein said transferrin derivative is obtained by: oxidation of a disulfide bond, cleavage of a disulfide bond with sulfite ion, or cleavage of a disulfide bond with a reducing agent, followed by S-alkylation;
   and wherein said albumin derivative is obtained by: oxidation of a disulfide bond, cleavage of a disulfide bond with sulfite ion, and cleavage of a disulfide bond with a reducing agent, followed by S-alkylation.

2. The thin membrane according to claim 1, which further comprises a protease inhibitor.

3. The thin membrane according to claim 1, which further comprises one or more kinds of colorants.

4. The thin membrane according to claim 3, which comprises a solid-dispersed or emulsion-dispersed colorant.

5. The thin membrane according to claim 1, which comprises a crosslinked transferrin derivative.

6. The thin membrane according to claim 1, wherein the transferrin derivative is a derivative in which a substituent is introduced on a sulfur atom derived from a disulfide bond.

7. The thin membrane according to claim 1, wherein the transferrin derivative is carboxymethyltransferrin.

8. The thin membrane according to claim 1, wherein the albumin derivative is a derivative in which a substituent is introduced on a sulfur atom derived from a disulfide bond.

9. The thin membrane according to claim 1, wherein the albumin derivative is one or more derivatives selected from the group consisting of carboxymethylated serum albumin, carboxymethylated conalbumin, and N-alkylsuccinimidated serum albumin.

10. The thin membrane according to claim 1, which has a thickness of 0.5–10 μm.

11. The thin membrane of claim 1, wherein said transferrin derivative is derived from human, bovine or swine transferrin, and wherein said albumin derivative is derived from human, bovine, swine, chicken, rabbit, rat, guinea pig, mouse, or equine albumin.

12. The thin membrane of claim 1, wherein said tranferrin derivative and/or said albumin derivative is obtained by oxidation of a disulfide bond with performic acid.

13. The thin membrane of claim 1, wherein said transferrin derivative and/or said albumin derivative is a S-sulfocysteine derivative.

14. A method for detecting MMP-7 protease activity, which comprises the steps of:
   (1) bringing a tissue slice or one or more cells into contact with a thin membrane; and
   (2) detecting a trace of digestion formed on the thin membrane by activity of MMP-7 protease;
   wherein said thin membrane comprises at least one substance selected from the group consisting of a transferrin derivative and an albumin derivative, wherein said substance is crosslinked and/or substantially water-insoluble;
   wherein said transferrin derivative is obtained by: oxidation of a disulfide bond, cleavage of a disulfide bond with sulfite ion, or cleavage of a disulfide bond with a reducing agent, followed by S-alkylation;
   and wherein said albumin derivative is obtained by: oxidation of a disulfide bond, cleavage of a disulfide bond with sulfite ion, and cleavage of a disulfide bond with a reducing agent, followed by S-alkylation.

15. The method according to claim 14, wherein the trace of digestion is detected after the thin membrane is washed.

16. The method according to claim 14, wherein the trace of digestion is detected after the thin membrane is stained with a dye.

17. The method according to claim 14, which further comprises the step of staining the tissue slice or the nuclei of the one or more cells with a dye of a color that enables distinction of the tissue slice or the cell nuclei from the thin membrane.

* * * * *